US00PP37460P2

(12) United States Plant Patent
Holtmaat

(10) Patent No.: US PP37,460 P2
(45) Date of Patent: Jun. 9, 2026

(54) ***NEPETA* PLANT NAMED 'NEPBP122'**

(50) Latin Name: ***Nepta* hybrid**
Varietal Denomination: NEPBP122

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/223,259

(22) Filed: May 30, 2025

(30) Foreign Application Priority Data

Feb. 19, 2025 (QZ) ..... PBR 2025/0350

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1, 258
CPC ... A01H 5/02; A01H 5/12; A01H 5/00; A01H 6/50
See application file for complete search history.

(56) References Cited

PUBLICATIONS

Floral Daily 2024 "This is the first time that we presented such a wide range of perennials already planted in the ground" retrieved on Aug. 18, 2025 at https://www.floraldaily.com/article/9658287/this-is-the-first-time-that-we-presented-such-a-wide-range-of-perennials-already-planted-in-the-ground/, 7 pp. (Year: 2024).*
Polish Nurserymen Association 2025 Nepeta Blue Planet retrieved on Aug. 18, 2025 at https://zszp.pl/en/plants/plant-novelties-competition-zszp/plant-novelties-competition-2025/nepeta-blue-planet-2/, 4 pp. (Year: 2025).*
YouTube video Flower Trials 2024 Vitroflora Highlights retrieved on Aug. 18, 2025 at https://www.youtube.com/watch?v=DYUtx17rBzU, one page. (Year: 2024).*

* cited by examiner

*Primary Examiner* — June Hwu
(74) *Attorney, Agent, or Firm* — Penny J. Aguirre

(57) ABSTRACT

A new cultivar of *Nepeta* named 'NEPBP122' that is characterized by its large flowers, its floriferous blooming habit, its compact plant habit, and its flowers that are purple in color.

2 Drawing Sheets

Botanical classification: *Nepeta* hybrid.
Variety Denomination: 'NEPBP122'.

CROSS REFERENCE TO A RELATED APPLICATION

This application claims priority to European Community Plant Variety Office (CPVO) Plant Breeder's Rights Application No. 2025/0350 filed on Feb. 19, 2025, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Nepeta* of hybrid origin and will be referred to hereafter by its cultivar name, 'NEPBP122'. 'NEPBP122' is an herbaceous perennial grown for landscape use.

'NEPBP122' derived from open pollination of unnamed and unpatented proprietary seedlings of *Nepeta* from the Inventor's breeding program in August of 2023. The collected seeds were pooled prior to showing and the exact parentage is therefore unknown. The new cultivar was selected from amongst the resulting seedlings as a single unique plant in August of 2023.

Asexual propagation of the new cultivar was first accomplished by the Inventor by tissue culture using meristematic tissue in March of 2024 in Zuidwolde, The Netherlands. Asexual propagation of the new cultivar by tissue culture and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'NEPBP122' as a unique cultivar of *Nepeta*.

1. 'NEPBP122' exhibits large flowers.
2. 'NEPBP122' exhibits a floriferous blooming habit.
3. 'NEPBP122' exhibits a compact plant habit.
4. 'NEPBP122' exhibits flowers that are purple in color.

'NEPBP122' can be compared to the cultivars *Nepeta* cultivars 'Walker's Low' (not patented) and 'Bokratune' (U.S. Plant Pat. No. 29,556). 'Walker's Low' is similar to 'NEPBP122' in having a compact plant habit and foliage color. 'Walker's Low' differs from 'NEPBP122' in having a taller plant height and flowers that are lighter purple in color. 'Bokratune' is similar to 'NEPBP122' in having flowers that are similar in color. 'Bokratune' differs from 'NEPBP122' in having a taller plant height, darker green foliage, and larger leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Alkemade Perennials, Vitroflora, Dobrepole, Podlewane, Nova Photo Graphik, Flower Trials (LinkedIn), I-SZTORM, and Herbariusz.

BRIEF DESCRIPTION OF THE DRAWINGS

The accompanying color photographs illustrate the overall appearance and distinct characteristics of a 6-month-old plant of the new *Nepeta* as grown in a 19-cm container in Boskoop, The Netherlands.

The photograph in FIG. 1 provides a side view of 'NEPBP122' in bloom.

Figure 1:
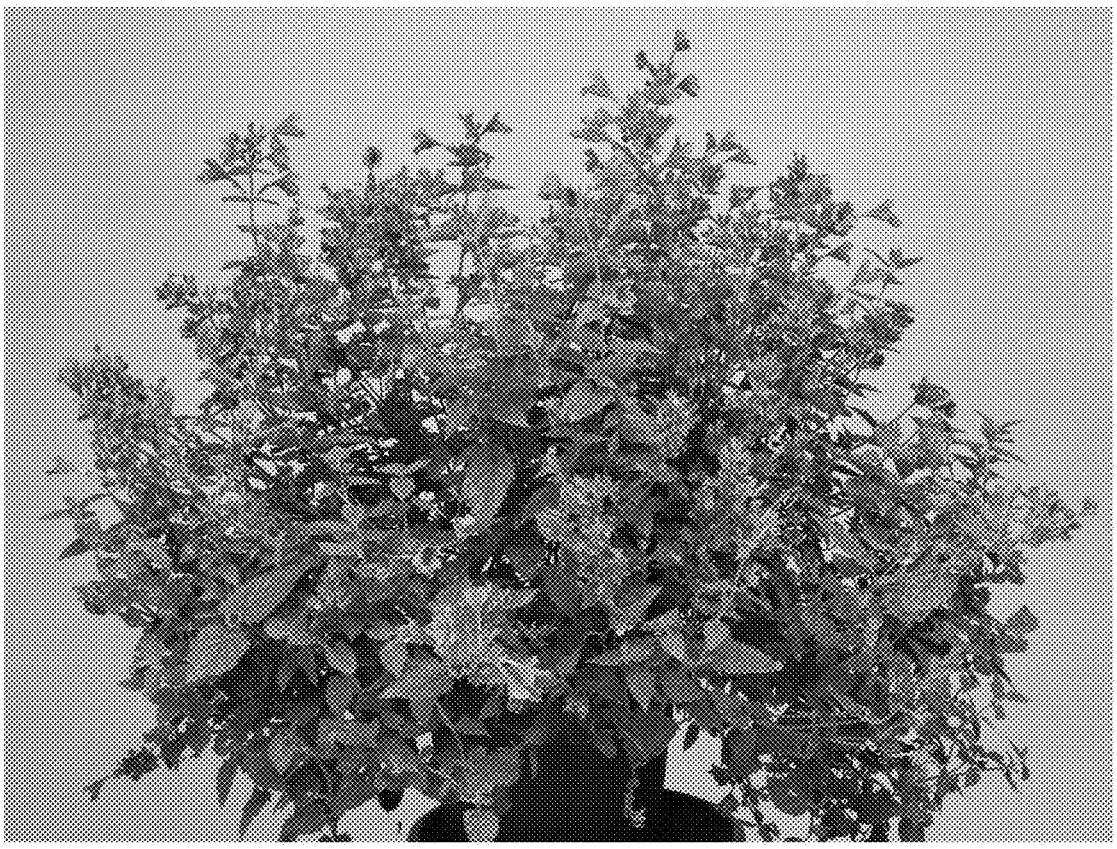
Figure 2:
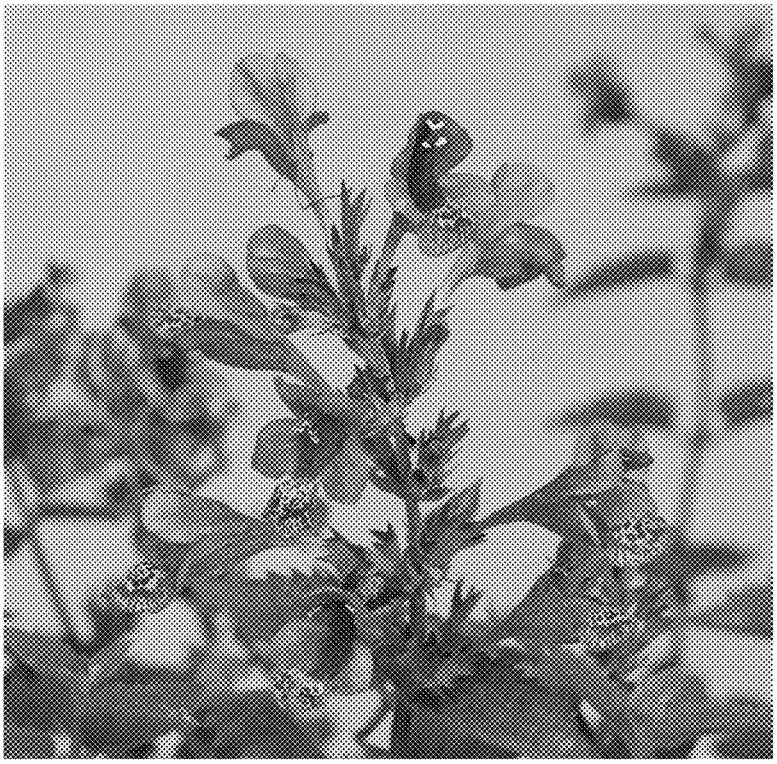

The photograph in FIG. 2 provides a close-up view of the flowers of 'NEPBP122'.

Figure 3:
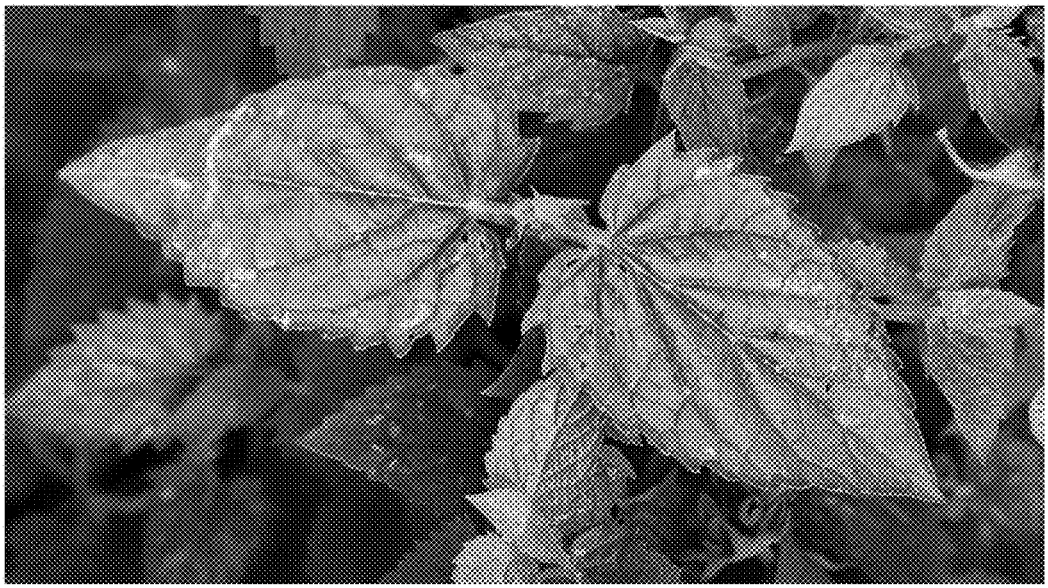

The photograph in FIG. 3 provides a close-up view of the foliage of 'NEPBP122'.

The colors in the photographs may differ slightly from the color values cited in the detailed botanical description, which accurately describe the colors of the new *Nepeta*.

DETAILED BOTANICAL DESCRIPTION

The following is a detailed description of the new cultivar of plants 6 months in age as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with the 2015 (2019 reprint) Colour Chart of The Royal Horticultural Society, London, England, except where general color terms of ordinary dictionary significance are used.

General description:

*Blooming period*.—June into September in the Netherlands, will rebloom in 5 to 6 weeks when cut back after flowering in early summer.

*Plant type*.—Herbaceous perennial.

*Plant habit*.—Broadly spreading, upright.

*Plant size*.—Average of 46 cm in height and 70 cm in diameter as a 6-month-old plant grown in a container.

*Hardiness*.—At least in U.S.D.A. Zones 5 to 9.

*Diseases and pests*.—No susceptibility or resistance to diseases or pests has been observed.

*Root description*.—Fibrous and fine.

*Root development*.—About 6 weeks to initiate roots and 2 months to produce a young rooted plant.

*Propagation*.—Stem cuttings (preferred) and tissue culture.

*Growth rate*.—High to moderately vigorous.

Stem description:

*Shape*.—Quadrangular.

*Stem color*.—Young stem; 145A, mature stems; 146C.

*Stem size*.—Average of 28.7 cm in length, 2.75 mm in diameter.

*Stem surface*.—Slightly glossy and densely covered with very short soft hairs; average of 0.5 mm in length and too small to measure color.

*Stem aspect*.—Held at varying angles an average of 35° to vertical, lateral branches held at an average of 20° to primary branch.

*Internode length*.—Average of 4.3 cm.

*Branching*.—Average of 10 primary branches and 8 lateral branches.

*Stem strength*.—Strong.

Foliage description:

*Leaf shape*.—Ovate.

*Leaf division*.—Simple.

*Leaf base*.—Truncate to nearly cordate.

*Leaf apex*.—Acute.

*Leaf venation*.—Pinnate, upper and lower surface color; 146B.

*Leaf margins*.—Serrate.

*Leaf arrangement*.—Opposite.

*Leaf attachment*.—Petiolate.

*Leaf surface*.—Upper surface; moderately rugose and slightly glossy, lower surface; slightly rugose and matte, both surfaces; moderately pubescent with very short hairs; an average of 0.3 mm in length and too small to measure color.

*Leaf size*.—Up to 4.6 cm in length and 2.9 cm in width.

*Leaf color*.—Young upper surface; 143B, young lower surface; 143C, mature upper surface; NN137B, mature lower surface; 146B and 148B.

*Leaf fragrance*.—Typical *Nepeta* scent when touched; moderately strong, pleasant and slightly minty.

*Petioles*.—An average of 1.1 cm in length and 1 mm in diameter, upper surface color 146B, lower surface color 146C, moderately strong, upper surface slightly glossy, lower surface moderately glossy, both surfaces moderately covered with very short pubescent hairs; an average of 0.3 mm in length and too small to measure color.

Inflorescence description:

*Inflorescence type*.—Terminal raceme of labiate flowers, individual flowers in oppositely placed clusters in an average of 5 whorls each holding about 8 individual flowers.

*Lastingness of inflorescence*.—Individual flowers average of 5 days, self cleaning.

*Inflorescence size*.—An average of 12.3 cm in height and 8.7 cm in diameter.

*Flower type*.—Labiate.

*Flower aspect*.—Outward.

*Flower number*.—Average of 40 per inflorescence, 1,000 per plant.

*Flower fragrance*.—None.

*Flower buds*.—Oblanceolate in shape, 1.5 cm in length, 5 mm in diameter, matte surface, color; 79B, immature calyx 145A and 145B, densely covered with very short hairs; an average of 0.3 mm in length and too small to measure color.

*Flower size*.—Average of 2.1 cm in height, 1.6 cm in diameter, 3.3 cm in length, throat 6 mm in diameter, tube 2.2 cm in length, tube 7 mm in diameter.

*Peduncle*.—Average of 4 mm in length, 1.5 mm in diameter, 144A and 144B in color, held straight in top of stem, strong, surface is matte and densely pubescent with short hairs; an average of 0.3 mm in length and too small to measure color.

*Pedicels*.—Average of 2 mm in length, 1 mm in diameter, 144B in color, held in an average angle of 35°, moderately strong in strength, surface is slightly glossy and densely pubescent with short hairs; an average of 0.3 mm in length and too small to measure color.

*Calyx*.—Rotate and tubular in shape, average of 1.2 cm in length and 4.5 mm in diameter.

*Sepals*.—5, rotate, base is fused 65%, narrow ovate in shape, entire margin, apex is narrow acute, campanulate arrangement, 1.2 cm in length, 1.5 mm in width, entire margins, upper surface is glabrous and smooth, lower surface is slightly glossy and matte, both surfaces are moderately pubescent with very short hairs; an average of 0.3 mm in length and too small to measure color, color: when opening and fully open upper surface; lower sepals 145A, veins 143A, lateral sepals and upper sepal 146C, veins 147A, when opening and fully open lower surface; lower sepals 145A, lateral sepals and upper sepal 146C, veined N187B.

*Petals*.—5, fused at base 75%, in 1 whorl, labiate, upper lobe; broadly ovate in shape, margin entire, apex broadly bluntly acute, 7 mm in length and 8 mm in width, based fused, upper and lower surface smooth and glabrous, non-rugose, lower lobe; spathulate in shape, margins finely irregular angulate and slightly undulate, apex of lower cleft into two lobes, base fused, 9 mm in length and 1 cm in width, base fused, upper and lower surface smooth, glabrous, matte, moderately pubescent with very short hairs on the lower surface an average of 1 mm in length and too small to measure color, throat and tube; inner and outer surfaces smooth and glabrous, tube; texture outer surface densely pubescent with very short hairs; an average of 0.3 mm in length and too small to measure color, color: two upper petal (lip) lobes; when opening upper surface N88B, when opening lower surface N88D, when fully open upper surface N88A to N88B, tips lightly flushed with 96B, veins N82B, fading to N82A and N82B, when fully open lower surface N88A, margins very lightly flushed with 96B, fading to N82C, lower petal (lip) lateral lobes; when opening upper surface N88B, when opening lower surface N88D, when fully open upper surface N88B, tips lightly flushed with 96B, veins N82B, fading to N82A and N82B, when fully open lower surface N88A, fading to N82C, lower petal (lip) central lobe: when opening upper surface N81A, heavily marbled with 84C and N80A, margins 85A, when opening lower surface N81B and N82B, when fully open upper surface N80A to N80B, heavily marbled with a blend of 85B, 85C, 86A, and N88B, margins a blend of N88B and 96B, fading to a blend of 76D and 90A, when fully open lower surface N81B and N82B, fading to N82B, corolla tube; inner surface 90B, outer surface 90B and 94B.

Reproductive organs:

*Gynoecium*.—Pistil; 1, 2.9 cm in length, style; 2.7 cm in length, 86A in color, stigma; cleft (2 parted), 1 mm in diameter and 86A in color, ovary; 152B in color.

*Androecium*.—Stamens; 4, filaments; 2 lower filaments average 1.1 cm, 2 upper filaments 1.2 cm, N88C, anthers; dorsifixed, narrow elliptic in shape, 1 mm in length, 0.5 mm in width, 99B in color, pollen; moderate to high in quantity and 156D in color.

*Fruit and seed*.—None have been observed to date.

It is claimed:

1. A new and distinct cultivar of *Nepeta* plant named 'NEPBP122' as herein illustrated and described.

* * * * *